United States Patent [19]

Davis

[11] Patent Number: 4,568,342

[45] Date of Patent: Feb. 4, 1986

[54] VARIABLE SIZE, REUSABLE DIAPER WITH FASTENER COVERS

[76] Inventor: Culley W. Davis, 157 E. 8180 South, Sandy, Utah 84070

[21] Appl. No.: 686,439

[22] Filed: Dec. 26, 1984

[51] Int. Cl.⁴ ............................................. A61F 13/16
[52] U.S. Cl. .................................................. 604/391
[58] Field of Search ................ 604/391, 390, 389, 385

[56] References Cited

U.S. PATENT DOCUMENTS

| | | | |
|---|---|---|---|
| 3,359,980 | 12/1967 | Rosenblatt | 604/391 |
| 3,653,381 | 4/1972 | Warnken | 604/391 |
| 4,402,690 | 9/1983 | Redfern | 604/391 |
| 4,410,327 | 10/1983 | Baggaley | 604/391 |

*Primary Examiner*—John D. Yasko

*Attorney, Agent, or Firm*—Thorpe, North & Western

[57] ABSTRACT

A variable-size, reusable diaper for infants comprises a back portion and a front portion, interconnected by an intermediate portion. First and second wing pieces project laterally from opposite sides of the back portion, with the wing pieces including respective first and second pile hook fasteners which overlapingly engage a pile loop fastener formed as a continuous strip on the front portion of the diaper. Such engagement is adjustable along the continuous strip fastener to permit the diaper to be adjusted to fit an infant's waist. First and second covers are formed on the outer side of the diaper on the first and second wing pieces respectively to alternatively cover or expose the first and second hook pile fasteners respectively.

11 Claims, 8 Drawing Figures

VARIABLE SIZE, REUSABLE DIAPER WITH FASTENER COVERS

BACKGROUND OF THE INVENTION

This invention relates to reusable diapers, and particularly to a variable-size diaper having integral pile hook and loop fasteners at least some of which may be covered when the diaper is being washed.

Pile hook and loop fasteners, such as those marketed under the name "Velcro", have been used on a variety of clothing articles including diapers. See, for example, C. L. Rosenblatt, U.S. Pat. No. 3,359,980 and H. V. Brooks et al, U.S. Pat. No. 3,081,772. Diapers which have utilized this type of fastener have proven to be fairly safe since the need for metal fasteners, such as safety pins, has been eliminated and thus the possibility of injury from such metal fasteners has been eliminated. Also, the pile hook and loop fasteners are relatively soft and flexible. Finally, the pile hook and loop fasteners are generally arranged so that the diaper waist size can be made adjustable to accommodate various size infants.

A problem in using the pile hook and loop fasteners on diapers which are intended for reuse is that upon washing, the pile hook fastener portion tends to engage and cling to the pile loop fastener portion so that the diaper may remain in a folded or partially folded position during washing. In such a position, the diaper cannot be cleaned as readily as if the diaper were in an unfolded position. Of course, fabric covers could be placed and pinned over the fasteners to prevent the engagement and clinging together of the fasteners, but this would be cumbersome, inconvenient and time consuming.

SUMMARY OF THE INVENTION

It is an object of the invention to provide a variable-size, reusable diaper which is convenient to use and clean.

It is another object of the invention to provide such a diaper which utilizes pile hook and loop fasteners arranged so that during washing or cleaning, the different fastener elements will not contact and cling to one another.

The above and other objects are realized in a specific illustrative embodiment of a variable-size, reusable diaper having an absorbent piece of material formed to include a back portion, a front portion, and an intermediate portion reduced in its width and connecting the front and back portions. First and second strips of pile hook fasteners are attached to the inner side of the diaper near opposite edges thereof and near the top edge of the back portion. One or more strips of pile loop fasteners are attached to the outer side of the diaper near the top edge of the front portion and positioned so as to engage and at least partially overlap the first and second fasteners when the diaper is placed on an infant. First and second pockets are formed on the outer side of the diaper opposite respective first and second fasteners so that when the pockets are turned inside-out, the pockets cover respective fasteners. The pockets are maintained right-side out when the diaper is placed on an infant so that the first and second hook fasteners will be exposed for engaging the loop fasteners. For washing or cleaning, the pockets are turned inside-out to cover the first and second hook fasteners so that they cannot contact the loop fasteners while being washed.

In other embodiments of the diaper of the present invention, the first and second strips are provided with covers of various shapes and types to prevent contact and clinging of the strips with other articles of clothing during washing or cleaning.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
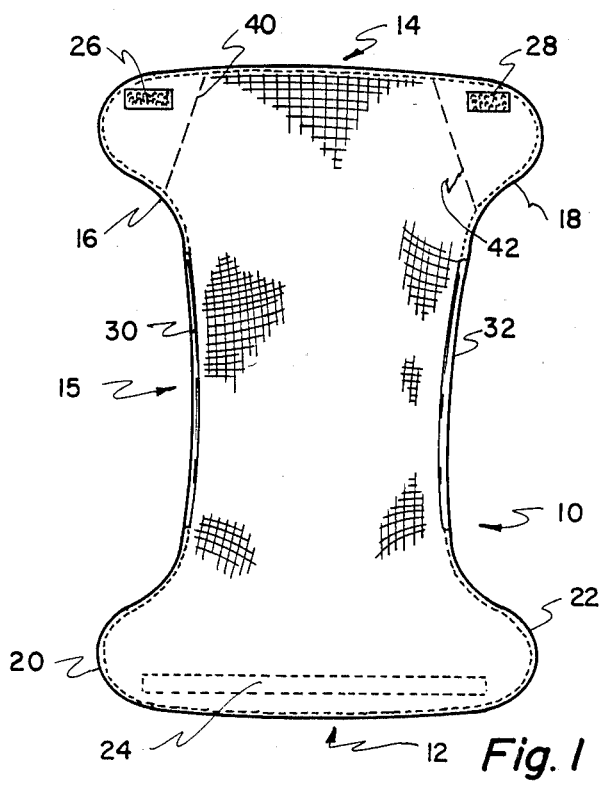
FIG. 1 is a plan view of the diaper of the present invention showing the contour thereof and the arrangement of pile hook and loop fasteners thereon.

Referring to FIG. 1, there is shown a diaper 10 formed from cotton cloth or other suitably absorbent material. The diaper comprises a front portion 12 and a back portion 14, with an intermediate seat portion 15 interposed therebetween. First and second wing pieces 16 and 18 project laterally from opposite sides of the back portion 14, while third and fourth wing pieces 20 and 22 project laterally from opposite sides of the front portion 12. The wing pieces 16 and 18, and 20 and 22 are integrally formed with the back portion 14 and front portion 12 respectively.

A pile loop fastener 24, formed as a continuous strip, is attached, such as by sewing, to the front portion 12 of the diaper along an imaginary line connecting the wing pieces 20 and 22. Preferably, the continuous strip fastener 24 is disposed on the outer side of the diaper so that it does not contact the infant's skin. In addition, the fastener 24 preferably extends the full length between the wing pieces 20 and 22 and onto the wing pieces.

Pile hook fastener strips 26 and 28 are attached, such as by sewing, to the wing pieces 16 and 18 respectively. These fastener strips 26 and 28 are preferably disposed on the inside of the diaper, with their respective longitudinal dimensions oriented along an imaginary line connecting the wing pieces 16 and 18. Furthermore, it is preferable that the fastener strips 26 and 28 extend from the outward edge of the wing pieces 16 and 18 respectively through at least a portion of the wing pieces, without extending onto the back portion 14.

Advantageously, elastic strips 30 and 32 are attached, such as by sewing, to the respective sides of the intermediate portion 15. These elastic strips 30 and 32 serve to gather the edges of the intermediate portion 15 in a conventional manner and provide elasticity to accommodate different size infants.

Figure 2:
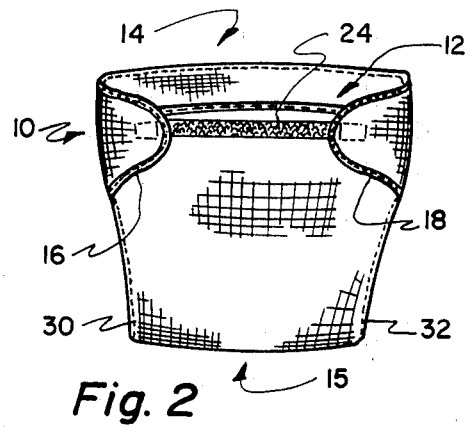
FIG. 2 is an elevation view of the diaper of the present invention folded to fit around an infant.

The diaper 10 is sized to be folded about an infant in the well known manner as shown in FIG. 2 with the front portion 12 contacting the infant's abdomen and the back portion 14 contacting the infant's lower back. The wing pieces 16 and 18 are folded over the wing pieces 20 and 22 so that the fastener strips 26 and 28 overlapingly engage the continuous fastener strip 24. The engagement of the fasteners 26 and 28 with the fastener 24 may be adjusted along the length of the fastener 24 to adjust the size of the diaper to fit the infant's waist.

The pile loop fastener strip 24 and the pile hook fastener strips 26 and 28 are preferably of the type commercially marketed under the name "Velcro", and manufactured by the Velcro Corporation of New York, N.Y. The fastener strip 24 is constructed of a soft, flannel-like surface having numerous looped fibers, and the fastener strips 26 and 28 are constructed of a plurality of coarse, bristle-like hook elements to engage and cling to the fastener strip 24. It is desirable that the softer loop fastener strip 24 be placed in the position shown on the front portion of the diaper since it will always generally be exposed except when adjusted to its minimum waist size. Any contact with the fastener strip 24 by an infant will generaly not cause irritation. When the diaper is in place, the coarse, bristle-like hook fastener strips 26 and 28 will be overlaping the fastener 24 and thus not be exposed to irritate the infant's skin.

The diaper of the present invention is designed to be reused after appropriate washing or cleaning. With the diaper construction described thus far, if the diaper were washed in a washing machine, it is possible that the fastener strips 26 and 28 might come in contact with the continuous fastener strip 24, cling to it and thereby hold the diaper in at least a partially folded position. In such a position, it is likely that the diaper would not be thoroughly cleaned or washed because some of the surfaces might not be suitably exposed to the water and cleaning agent.

To avoid the problem of the fastener strips 26 and 28 possibly engaging and clinging to the fastener strip 24 during washing, a pair of pockets 40 and 42 are provided on the outer side of wing pieces 16 and 18 respectively. Each of the pockets 40 and 42 is made of a piece of fabric attached, such as by sewing, at a portion of its outer periphery to a corresponding portion of the periphery of a respective wing piece. That is, the outer periphery of each pocket fabric piece is shaped to be generally coincident with the periphery of the respective wing when placed thereover. The edges can then be simply sewn together.

Figure 3:
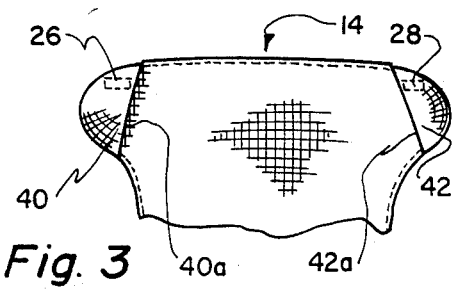
FIG. 3 is a fragmented plan view of the diaper of FIG. 1 showing the two pockets formed on the wing pieces of the back portion of the diaper folded inside-out to cover the two pile hook fasteners.

The inner edges 40a and 42a of the pockets 40 and 42 respectively are not attached to the diaper but rather form inwardly and downwardly facing openings for the pockets as best seen in FIG. 3. FIG. 1 shows the dotted line representation of the pocket since the pockets are formed on the outer side of the diaper which, in FIG. 1, is not seen. FIG. 3 shows the pockets 40 and 42 turned inside-out to cover the fastener strips 26 and 28. In this position, the diaper would be ready for washing since the fastener strips 26 and 28 would be "tucked" into respective pockets 40 and 42 and thus would not engage and cling to the fastener strip 24.

Figure 4A:
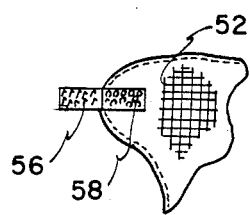
FIGS. 4A and 4B show fragmented open and closed views respectively of an alternative embodiment of diaper fasteners and covers.
Figure 4B:
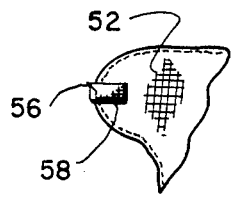

FIGS. 4A and 4B show fragmented views of an alternative embodiment of diaper fasteners and covers made in accordance with the present invention. Depicted in the FIGS. is a back portion wing piece 52 (similar to the piece 16 of FIGS. 1 and 2). The rest of the diaper to which the wing piece 52 is connected is the same as the diaper of FIGS. 1-3 except that the other back portion wing piece (not shown in FIGS. 4A & 4B) is a mirror image of the piece 52.

Attached to the inner side of wing piece 52 near an outer edge thereof is a pile hook fastener strip 56 of flexible material which extends laterally from the wing piece. A pile loop fastener strip 58 is attached to the wing piece 52 contiguous with the strip 56 and positioned so that when the strip 56 is folded over onto the wing piece (FIG. 4B), it contacts and adheres to the strip 58. When in this "closed" position, the pile hook strip 56 is not exposed to engage and cling either to the pile loop fastener of the diaper (not shown) or other articles of clothing.

Figure 5A:
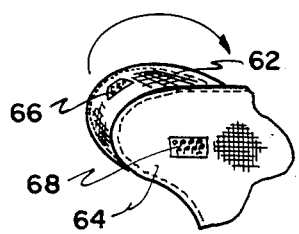
FIGS. 5A and 5B show fragmented open and closed views respectively of still another embodiment of the present invention.
Figure 5B:
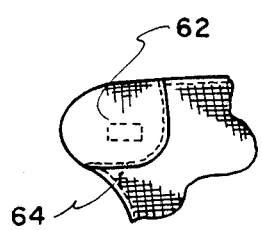

FIGS. 5A and 5B show another embodiment of diaper fasteners and covers which includes a flap 62 attached at one edge to the rear-side edge of a back portion wing piece 64 of a diaper. Attached to the inside surface of the flap 62 is a pile loop fastener strip 66. Attached to the wing piece 64 is a pile hook fastener 68 positioned so that when the flap 62 is folded over the wing piece 64, the strip 66 will overlie, contact and adhere to the strip 68 (FIG. 5B).

Figure 6:
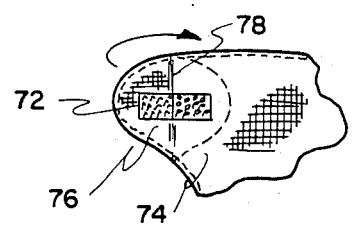
FIG. 6 shows a fragmented view of a further embodiment of diaper fasteners and covers.

Finally, FIG. 6 shows still another embodiment of the present invention. This embodiment includes a pile hook fastener strip, shown by dotted line 72, attached to a back portion wing piece 74. A cover piece 76 is attached at its edge to the wing piece 74 to cover the fastener strip 72. A portion of the edge of the cover 76 is coterminous with a portion of the edge of the wing piece 74. Formed in the cover piece 76 is a slit opening 78 positioned over the fastener strip 72 to allow access thereto. When the diaper is not being worn, the slit opening 78 is substantially closed to cover the fastener strip 72. When the diaper is placed on an infant, the slit opening 78 is opened to expose at least a portion of the fastener strip 72 to enable engagement of the strip with the corresponding pile loop fastener strip.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A variable-size, reusable diaper comprising an absorbent piece of material formed to include
    a back portion having first and second wing pieces projecting laterally from respective opposite sides of said back portion, said first and second wing pieces each having respective first and second pile fastening means attached thereto on the inner side of the diaper,
    a front portion having third and fourth wing pieces projecting laterally from respective opposite sides thereof in the same direction as said first and second wing pieces respectively, said front portion having third pile fastening means attached thereto on the outer side of the diaper on the third and fourth wing pieces,
    an intermediate portion interposed between said front and back portions,
    said third pile fastening means being positioned so as to engage and at least partially overlap the first and second pile fastening means when the diaper is placed on an infant, and first and second cover elements disposed on the first and second wing pieces respectively and moveable to selectively cover the first and second pile fastening means respectively, or to expose same.

2. A diaper as in claim 1 wherein said first and second cover elements comprise first and second pockets formed on the outer side of the first and second wing pieces respectively so that when the pockets are turned inside out, the pockets cover the first and second pile fastener means respectively.

3. A diaper as in claim 2 wherein each of said pockets is formed of a piece of fabric attached at a portion of its periphery to a corresponding portion of the periphery of a respective wing piece of the back portion so that the opening of said each pocket faces inwardly and downwardly.

4. A diaper as in claim 3 wherein said first and second pile fastening means comprise strips of pile hook fasteners, and wherein said third pile fastening means comprises a single, continuous strip of pile loop fasteners oriented along an imaginary line connecting said third and fourth wing pieces.

5. A diaper as in claim 1 wherein said first and second cover elements comprise first and second flaps attached to the first and second wing pieces respectively, and foldable to cover the first and second pile fastening means respectively, said first and second flaps including fourth and fifth pile fastening means respectively for engaging and adhering to the first and second pile fastening means respectively when the flaps are folded over the wing pieces.

6. A diaper as in claim 5 wherein said first and second pile fastening means comprise strips of pile hook fasteners, wherein said third pile fastening means comprises a single, continuous strip of pile loop fasteners oriented along an imaginary line connecting said third and fourth wing pieces, and wherein said fourth and fifth pile fastening means comprise strips of pile loop fasteners.

7. A diaper as in claim 1 wherein said first and second cover elements comprise first and second flexible cover patches attached to their perimeters to the first and second wing pieces respectively to cover the first and second pile fastening means respectively, each of said cover patches including a slit opening disposed over the respective pile fastening means and being openable to expose the pile fastening means.

8. A diaper as in claim 7 wherein said first and second pile fastening means comprise strips of pile hook fasteners, and wherein said third pile fastening means comprises a single, continuous strip of pile loop fasteners oriented along an imaginary line connecting said third and fourth wing pieces.

9. A variable-size, reusable diaper comprising an absorbent piece of material formed to include a back portion having first and second wing pieces projecting laterally from respective opposite sides of said back portion, said first and second wing pieces each having respective first and second pile fastening means attached thereto at the inner side of the diaper to project laterally outwardly, respective fourth and fifth pile fastening means attached thereto on the inner side of the diaper inwardly adjacent to the first and second pile fastening means respectively, and said first and second pile fastening means being foldable to overlie, engage and adhere to the fourth and fifth pile fastening means respectively, a front portion having third and fourth wing pieces projecting laterally from respective opposite sides thereof in the same direction as said first and second wing pieces respectively, said front portion having third pile fastening means attached thereto on the outer side of the diaper on the third and fourth wing pieces, an intermediate portion interposed between said front and back portions, and said third pile fastening means being positioned so as to engage and at least partially overlap the first and second pile fastening means when the diaper is placed on an infant.

10. A diaper as in claim 9 wherein said first and second pile fastening means comprise strips of pile hook fasteners, wherein said third pile fastening means comprises a single, continuous strip of pile loop fasteners oriented along an imaginary line connecting said third and fourth wing pieces, and wherein said fourth and fifth pile fastening means comprise strips of pile loop fasteners.

11. A variable-size, reusable diaper comprising an absorbent piece of material formed to include a back portion, a front portion, an intermediate portion reduced in its width connecting the front and back portions, first and second strips of hook fasteners attached to the inner side of the diaper near opposite edges thereof and near the top edge of the back portion, first and second cover elements formed on the diaper adjacent the first and second fasteners respectively to selectively cover or expose respective fasteners, and one or more strips of loop fasteners attached to the outer side of the diaper near the top edge of the front portion and positioned so as to engage and at least partially overlap the first and second fasteners when the diaper is placed on an infant.

* * * * *